United States Patent [19]

Sharpless et al.

[11] Patent Number: 4,946,974

[45] Date of Patent: Aug. 7, 1990

[54] OPTICALLY ACTIVE DERIVATIVES OF GLYCIDOL

[75] Inventors: Karl B. Sharpless, Brookline; Janice M. Klunder, Somerville, both of Mass.; Tetsuo H. Onami, Fukushima, Japan

[73] Assignee: Massachusetts Institute of Technology, Cambridge, Mass.

[21] Appl. No.: 913,936

[22] Filed: Oct. 1, 1986

[51] Int. Cl.$^5$ ............................................ C07D 303/16
[52] U.S. Cl. .................................... 549/551; 549/539; 549/555; 549/556
[58] Field of Search ................. 549/551, 555, 556, 539

[56] References Cited

U.S. PATENT DOCUMENTS

| | | |
|---|---|---|
| 2,755,290 | 7/1956 | Mueller et al. |
| 3,290,336 | 12/1966 | McClure et al. |
| 4,210,653 | 7/1980 | Baldwin et al. ........... 546/330 |
| 4,346,042 | 8/1982 | Baldwin et al. ........... 549/557 |
| 4,471,130 | 9/1984 | Katsuki et al. ........... 560/218 |

FOREIGN PATENT DOCUMENTS

| | | | |
|---|---|---|---|
| 0071251A1 | 2/1983 | European Pat. Off. ......... 549/551 |
| 0157623A | 10/1985 | European Pat. Off. ......... 549/551 |

OTHER PUBLICATIONS

Szabo et al., "Some Alkyl Esters of, etc.", CA 14593d, (1957).
Mishima et al., "Living Group Effects of the, etc.", *Mem. of the Fac. of Science*, 14, 199, (1983).
Pierre J. et al., Bull Soc. Chim. Fr:2868, (1969).
Chantemps, P. et al., C. R. Acad. Sci. Paris Ser C 266:622, (1968).
Nakabayashi, N. et al., Bull, Chem. Soc. Jpn. 39:413, (1966).
Ichikawa, K. CA 61:7008d, (1964).
Cornforth et al., J. Chem. Soc., (1959)112.
Chiral Building Blocks Art., 12/13/85, Journ. of Org. Chem:50, 25.
McClure et al., Journ. Amer. Chem. Soc. 101:13, (6/20/79(, p. 3666.
Norman Metger, Mosaic 16:1, 34, (1/2/85).
Sharpless, K. B., Chem. In Britain, 22:1, 37, (1/86).

*Primary Examiner*—Richard L. Raymond
*Assistant Examiner*—Patricia L. Morris
*Attorney, Agent, or Firm*—George E. Neuner; Ronald I. Eisenstein

[57] ABSTRACT

Optically active derivatives of glycidol are disclosed. These compounds, (2S) and (2R) glycidyl tosylate and (2S) and (2R) glycidyl 4-chloro-3-nitrobenzenesulfonate can be readily crystallized to high enantiomeric purity. Their use in other synthesis reactions is also described.

8 Claims, No Drawings

OPTICALLY ACTIVE DERIVATIVES OF GLYCIDOL

The Government has rights in this invention pursuant to Grant Number NIH-5-R01-GM28384 awarded by the Department of Health and Human Services.

Optically active compounds have increasingly gained importance as the ability to manipulate the synthesis of other optically active compounds has improved. A compound is optically active if its atoms are not superimposable upon those of its mirror image. Isomers that are mirror images of each other are called enantiomers. Enantiomers have the same physical properties except for this difference in geometrical shape, i.e. mirror image. This difference however, has important consequences.

In living systems only one form of the stereoisomer generally functions properly. The other form typically either has no biological function or results in harm. In nature, the desired enantiomer is naturally synthesized. Synthetic chemists, in contrast, have rarely been as successful in making a pure enantiomer. They generally obtain racemic mixtures containing equal amounts of both optical forms of the molecule, i.e. dextrarotary (right-handed) and levorotary (left-handed). Consequently, these racemic mixtures do not exhibit properties based upon optical activity.

Obtaining asymmetric molecules has traditionally involved physically or chemically resolving the desired molecule from a racemic mixture of the two different optical forms. A second method, the chiral pool method, involves using naturally occurring asymmetric molecules as building blocks for the desired asymmetric molecule. A third method has been developed which involves controlling the steps of the reaction so that only the desired enantiomer is produced (See U.S. Pat. No. 4,471,130).

While the latter method has resulted in a tremendous advance in the field, problems still remain. The control over the reaction process is often not complete, and both forms of the molecule can still be produced. Even a small amount of the undesired form of the enantiomer results in significant loss of optical purity in the resultant mixture because an equal amount of the desired form of the enantiomer is associated with the undesired form. Thus, a step which produces 90% of the desired enantiomer only results in 80% enantiomeric excess (% e.e.).

The titanium-catalyzed asymmetric epoxidation of allylic alcohols has been important in further refining the above-described controlled step process. Homochiral glycidol has been useful in the synthesis of β-adrenergic blocking agents (β-blockers).

However, glycidol is difficult to store and isolate because it is unstable. The in situ derivation of glycidol where the unstable glycidol is derivatized after completion of the assymmetric epoxdiation reaction rather than isolated directly from the reaction mixture has many benefits. The derivatives are easier to handle, and they are more advanced synthetic intermediates than the parent glycidol. However, the ability to obtain high enantiomeric purity for these glycidol derivatives can vary greatly.

In substitution reactions of these derivatives poor regioselectivity results in a substantial deterioration in the optical purity of the starting material. Consequently, it is desirable to find derivatives which approach optical purity, and which exhibit high regioselectivity in substitution reactions.

We have now discovered two such compounds that are stable and can reach high enantiomeric purity. The two compounds are glycidyl tosylate and glycidyl 4-chloro-3-nitrobenzenesulfonate. With recrystallization it is possible to obtain enantiomeric-purities in excess of 90%, and thus far, for the glycidyl tosylate up to about 98% e.e.

Although racemic mixtures of glycidyl tosylate have been reported (Pierre, J. et al. *Bull. Soc. Chim. Fr.:* 2868 (1969); Chantemps, P. et al., *C.R. Acad. Sci., Paris, Ser. C,* 266:622 (1968); Nakabayashi, N., et al, *Bull. Chem. Soc. Jpn.,* 39:413 (1966); Ichikawa, K., *Yuki Gosei Kagaku Kyokai Shi,* 22:553 (1964)), we have now found that (2S) or (2R) glycidyl tosylate can readily be produced from allylic alcohol, and crystallized to high enantiomeric purity.

The glycidyl tosylate compound is produced by the following reaction schemes:

A. GLYCIDYL TOSYLATE

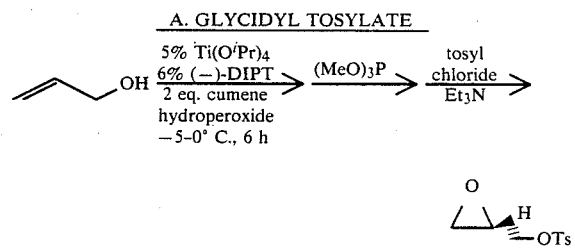

The (2S)-glycidyl tosylate preferably is purified to at least about 90% e.e., and even more preferably at least about 94% e.e, and most preferably about 98.0% e.e. Optical yields up to about 98.0% e.e. have been obtained in accord with this invention. Purification is obtained by using crystallization techniques which are well known in the art.

(2R)-glycidyl tosylate can be similarly produced by using (+)-DIPT instead of (−)-DIPT. (2R) compounds can be purified to the same enantiomeric purity as (2S) compounds.

The (2S)-glycidyl 4-chloro-3-nitrobenzenesulfonate is similarly produced as shown in the following reaction scheme:

B. GLYCIDYL 4-CHLORO-3-NITROBENZENESULFONATE

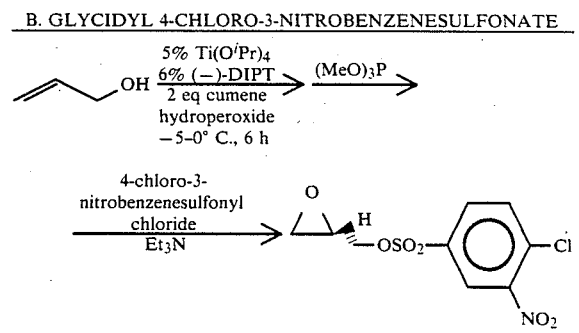

This compound is preferably purified to at least about 90% e.e. and even more preferably to at least about 94% e.e. The (2R) compound can be purified to the same enantiomeric purity as the (2S) compound and is obtained by using (+)-DIPT instead of (−)-DIPT.

The crystallized compound is stable and can easily be stored at room temperature until its use is desired. The stability of those compounds means that they can be used commercially as "starting materials" in the synthesis of, for example, β-blockers. For example, a convenient, one-pot procedure can be employed to convert the glycidyl p-toluenesulfonate into an important intermediate to the β-blocker, propranolol, which can be converted to propranolol by the addition of $^i$PrNH$_2$ and H$_2$O in the reaction mixture.

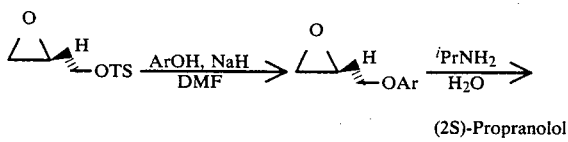

(2S)-Propranolol

This substitution reaction takes place with high regioselectivity, about 97:3 (C$_1$:C$_3$).

Other intermediates to β-blockers, or related compounds can be readily made according to the following reaction scheme:

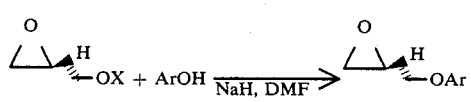

where X is tosylate or 4-chloro-3-nitrobenzenesulfonate, and ArOH is an aromatic alcohol. Any aromatqic alcohol capable of displacing the sulfonate moiety can be used in the reaction to create the desired intermediate. Preferable aromatic alcohols are those that yield desired β-blockers upon subsequent reaction with a predetermined amine. The appropriate amine to use can be readily determined by the person of ordinary skill in the art.

The invention will be further illustrated by the examples that follow:

General

Crushed 3 Å molecular sieves (Aldrich Chemical Co.) were activated by heating in a vacuum oven at 160° C. and 0.05 mm Hg for at least 8 hours. Diisopropyl tartrate and titanium (IV) isopropoxide (Aldrich) were distilled under vacuum and were stored under an inert atmosphere. Allyl alcohol and cumene hydroperoxide (tech., 80%, Aldrich) were dried prior to use over 3 Å molecular sieves, but otherwise used as received. Dichloromethane (EM Reagent) was not distilled, but was also dried over 3 Å molecular sieves. 1-Naphthol (Aldrich) was sublimed prior to use.

Melting points were determined on a Thomas Hoover capillary melting point apparatus and are uncorrected. IR spectra were recorded on a Perkin-Elmer 597 spectrophotometer. $^1$H NMR spectra were recorded on a Bruker WM-250 (250 MHz) spectrometer with tetramethylsilane as an internal standard.

EXAMPLE 1

Preparation of (2S)-Glycidyl Tosylate an oven-dried 4-l three-necked flask equipped with a mechanical stirrer, low-temperature thermometer, Claisen adapter, nitrogen inlet and rubber septum, was charged with activated 3 Å powdered sieves (35 g) and 1.9 l dichloromethane. D-(—)Diisopropyl tartrate (14.0 g, 0.06 mol) was added via cannula as a solution in 15 ml CH$_2$Cl$_2$, washing with an additional 10 ml CH$_2$Cl$_2$. Allyl alcohol (68.0 ml, 58.1 g, 1.0 mol) was then added, the mixture cooled to −5° C. under nitrogen, and Ti(OiPr)$_4$ (15.0 ml, 14.3 g, 0.05 mol) added via syringe. After stirring for 30 minutes, precooled (ice bath) cumene hydroperoxide (80%, 350 ml, ca. 2 mol) was added via cannula over a period of one hour, maintaining an internal temperature of ≦−2° C. The reaction mixture was stirred vigorously under nitrogen at −5 to 0° C. for six hours. After cooling to −20° C. trimethyl phosphite was added very slowly via cannula, not allowing the temperature to rise above −10° C., and carefully monitoring the reduction of hydroperoxide [TLC in 40% EtOAc/hex; tetramethyl phenylenediamine spray indicator (1.5 g in MeOH:H$_2$O:HOAc 128:25:1 ml); ca. 141 ml (148.9 g, 1.2 moles) of P(OMe)$_3$ were required for complete reduction. Further excess should be avoided.] The reaction is quite exothermic and addition took one hour. Triethylamine (175 ml, 127 g, 1.26 mol) was then added, followed by addition of p-toluenesulfonyl chloride (220.4 g, 1.05 mol) as a solution in 250 ml dichloromethane. The flask was stoppered and transferred to a freezer at −20° C.

After 10 hours the reaction mixture was allowed to warm gradually to room temperature, then filtered through a pad of Celite, washing with additional dichloromethane. The resultant yellow solution was washed with 10% tartaric acid, followed by saturated brine, dried (MgSO$_4$) and concentrated to afford an oil, from which volatile components (e.g. cumene, 2-phenyl-2-propanol, P(OMe)$_3$, OP(OMe)$_3$, etc.) were removed under high vacuum at 65° C. on a rotary evaporator equipped with a dry ice condenser. The residue was filtered through a short pad of silica gel (ca. 1 g per g crude oil), eluting with dichloromethane. Concentration gave a lemon yellow oil (193.5 g), which was dissolved in ca. 175 ml warm Et$_2$O and crystallized by addition of pet. ether and cooling, seeding with pure material. Seed crystals may be obtained by purifying a small portion of the crude oil by column chromatography (silica gel). The resulting off-white solid was recrystallized twice (Et$_2$O-pet ether), seeding each time with pure material. (2S)-Glycidyl tosylate was obtained as large white prisms (91.7 g, 40%); mp 46°-48.5° C.; $[\alpha]_D^{25} +17.5°$ (c=2.13, CHCl$_3$), 94% ee.

Attempts to measure the e.e. directly, via $^1$H NMR in the presence of chiral shift reagents, or by HPLC on a chiral stationary phase, proved unsuccessful. Therefore, glycidyl tosylate was converted to the corresponding iodohydrin, following Conforth's published procedure (J. Chem. Soc. (1959), 112). The crude iodohydrin was then directly esterified with (R)-(+)-α-methoxy-α-(trifluoromethyl) phenylacetyl chloride to give the Mosher ester, and the e.e. measurement was made by HPLC of the ester on a chiral Pirkle column, eluting with 8% iso-proponalol/hexane. The e.e. was also determined by $^1$H NMR analysis of the Mosher ester in C$_6$D$_6$.

IR (KBr) 3075, 3000, 2935, 1598, 1495, 1448, 1405, 1362, 1310, 1295, 1257, 1195, 1180, 1098, 1020, 965, 915, 875, 666, 575, 558 cm$^{-1}$. NMR (250 MHz, CDCl$_3$) δ 7.81 (d, J=8 Hz, 2H), 7.36 (d, J =8 Hz, 2H), 4.26 (dd, J=3.4, 11.4 Hz, 1H), 3.95 (dd, J=6.0, 11.4 Hz, 1H), 3.16-3.23 (m, 1H), 2.82 (t, J=4.5 Hz, 1H), 2.60 (dd, J=2.5, 4.75 Hz, 1H), 2.46 (s, 3H). Anal. Calcd for C$_{10}$H$_{12}$O$_4$S: C, 52.62; H, 5.30. Found: C, 52.75; H, 5.29.

By using the above described procedure glycidyl tosylate having enantiomeric purity up to 98.0% e.e. has been obtained.

EXAMPLE 2

Preparation of (2S)-Propanolol from (2S)-Glycidyl Tosylate

In a 250-ml round-bottomed flask equipped with a rubber septum, sodium hydride (oil free, 1.15 g, 0.048 mol) was suspended in DMF (40 ml, stored over 3 Å sieves) at room temperature under a nitrogen atmosphere. 1-Naphthol (6.06 g, 0.042 mol) was added via cannula as a solution in DMF (20 ml) to produce a foamy green sludge. After 15-30 minutes, a solution of (2S)-glycidyl tosylate (94% ee, from Example 1, 9.138 g, 0.040 mol) in DMF (20 ml) was added via cannula. A clear green-brown solution resulted.

After 4 hours the reaction was judged to be complete by TLC (40% EtOAc/hex). Isopropylamine (34 ml, 0.4 mol) and water (3.4 ml, 0.19 mol) were added, the septum replaced with a cold water condenser, and the reaction was heated to reflux (bath temperature was about 90° C.) The reaction was followed by TLC (50% $CH_2Cl_2$/hex). After 4 hours the heat was removed, the reaction mixture diluted with water (100 ml) and extracted with ether (3×100 ml). The combined organic extracts were washed with 1N NaOH, saturated brine, dried over $Na_2SO_4$ and concentrated under reduced pressure. Overnight drying in vacuo afforded a yellow solid (9.75 g).

This solid was dissolved in ether (100 ml), treated with gaseous HCl, and the resulting white solid (10.62 g) collected by suction filtration. Recrystallization from methanol-ether afforded 7.11 g (60%) of (2S)-propranolol hydrochloride as white crystals, mp 192°-193.5° C.; $[\alpha]^{21} -25.7°$ (c=1.23, EtOH). Anal. Calcd for $C_{16}H_{22}ClNO_2$: C, 64.96: H, 7.50; N, 4.74. Found: C, 64.76; H, 7.61; N, 4.66. 1.5 g of slightly off-white crystals were obtained as a second crop. Recrystallization afforded an additional 1.18 g (10%) of propranolol hydrochloride, mp 191.5°-194° C.; $[\alpha]_D^{21} -26°$ (c=0.94, EtOH).

EXAMPLE 3

Preparation of (2S)-glycidyl 4-chloro-3-nitrobenzenesulfonate (2S)-Glycidyl 4-chloro-3-nitrobenzenesulfonate was prepared using 4-chloro-3-nitrobenzenesulfonyl chloride instead of p-toluenesulfonyl chloride, according to the method described in Example 1. Crude crystals (mp 49°-54° C., 41% yield) which were obtained by the crystallization of an oil from diethyl ether-pet. ether mixture, were recrystallized from ethanol-ethyl acetate mixture to give pure crystals, mp 54.7°-55.2° C., 94% e.e.

The preparation of the Mosher ester and the ee measurement of the ester were made according to the method described in Example 1.

IR(KBr) 3105, 3015, 1605, 1573, 1541, 1400, 1385, 1363, 1339, 1252, 1197, 1190, 1170, 1159, 1107, 1056, 995, 979, 963, 945, 922, 914, 899, 868, 842, 779, 767, 759, 670, 647, 591, 576, 533, 494, 452, cm$^{-1}$.

NMR (250 MHz, CDl$_3$) δ 8.43 (d, J=2 Hz, 1H), 8.05 (dd, J=2.1, 8.5 Hz, 1H), 7.79 (d, J=8.5, 1H) 4.51 (dd, J=2.8, 11.6 Hz, 1H) 4.04 (dd, J=6.5, 11.6 Hz, 1H) 3.23 (m, 1H), 2.87 (t, J=4.5, 4.5 Hz, 1H), 2.6 (dd, J=2.5, 4.4 Hz, 1H).

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

We claim:

1. A compound of the formula

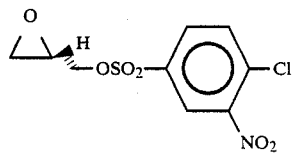

produced from allylic alcohol and recrystallized to high enantiomeric purity.

2. The compound of claim 1 purified to at least about 90% e.e.

3. The compound of claim 1 purified to at least about 94% e.e.

4. A compound of the formula:

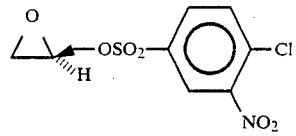

produced from allylic alcohol and recrystallized to high enantiomeric purity.

5. Th compound of claim 4 purified to at least about 90% e.e.

6. The compound of claim 4 purified to at least 94% e.e.

7. A compound of the formula

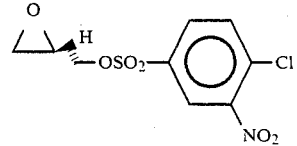

produced from a mixture containing its enantiomer wherein the compound has been recrystallized to an optical purity of at least about 94% e.e.

8. A compound of the formula

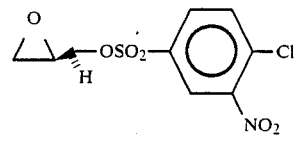

produced from a mixture containing its enantiomer wherein the compound has been recrystallized to an optical purity of at least about 94% e.e.

* * * * *